(12) United States Patent
Dogdas et al.

(10) Patent No.: US 11,494,907 B2
(45) Date of Patent: Nov. 8, 2022

(54) SYSTEMS AND METHODS FOR PROCESSING ELECTRONIC IMAGES FOR COMPUTATIONAL ASSESSMENT OF DISEASE

(71) Applicant: PAIGE.AI, Inc., New York, NY (US)

(72) Inventors: Belma Dogdas, Ridgewood, NJ (US); Christopher Kanan, Rochester, NY (US); Thomas Fuchs, New York, NY (US); Leo Grady, Darien, CT (US); Kenan Turnacioglu, New York, NY (US)

(73) Assignee: PAIGE.AI, INC., New York, NY (US)

( * ) Notice: Subject to any disclaimer, the term of this patent is extended or adjusted under 35 U.S.C. 154(b) by 0 days.

(21) Appl. No.: 17/123,658

(22) Filed: Dec. 16, 2020

(65) Prior Publication Data

US 2021/0209753 A1 Jul. 8, 2021

Related U.S. Application Data

(60) Provisional application No. 62/957,523, filed on Jan. 6, 2020.

(51) Int. Cl.
*G06T 7/00* (2017.01)
*G06T 7/11* (2017.01)
*G06V 20/69* (2022.01)

(52) U.S. Cl.
CPC .............. *G06T 7/0012* (2013.01); *G06T 7/11* (2017.01); *G06V 20/698* (2022.01);
(Continued)

(58) Field of Classification Search
CPC .. G06T 7/0012; G06T 7/0011; G06K 9/00147
See application file for complete search history.

(56) References Cited

U.S. PATENT DOCUMENTS

| 7,761,240 B2 * | 7/2010 | Saidi | G06V 20/695 |
| | | | 382/128 |
| 8,227,202 B2 * | 7/2012 | Fantl | G01N 33/5073 |
| | | | 435/6.14 |

(Continued)

OTHER PUBLICATIONS

W. Fantl etl al. , "U.S. Appl. No. 61/048,886" "Methods of Determining the Health Status of an Individual", 2008 (Year: 2008).*

(Continued)

*Primary Examiner* — Gandhi Thirugnanam
(74) *Attorney, Agent, or Firm* — Bookoff McAndrews, PLLC (57) ABSTRACT

Systems and methods are disclosed for receiving a digital image corresponding to a target specimen associated with a pathology category, wherein the digital image is an image of tissue specimen, determining a detection machine learning model, the detection machine learning model being generated by processing a plurality of training images to output a cancer qualification and further a cancer quantification if the cancer qualification is an confirmed cancer qualification, providing the digital image as an input to the detection machine learning model, receiving one of a pathological complete response (pCR) cancer qualification or a confirmed cancer quantification as an output from the detection machine learning model, and outputting the pCR cancer qualification or the confirmed cancer quantification.

15 Claims, 8 Drawing Sheets

(52) U.S. Cl.
CPC .............. *G06T 2207/10056* (2013.01); *G06T 2207/20081* (2013.01); *G06T 2207/20084* (2013.01); *G06T 2207/30024* (2013.01)

(56) References Cited

U.S. PATENT DOCUMENTS

| | | | | |
|---|---|---|---|---|
| 10,176,408 | B2* | 1/2019 | Paik | G06V 20/698 |
| 10,650,929 | B1* | 5/2020 | Beck | G16H 30/40 |
| 10,891,550 | B2* | 1/2021 | Kapur | G06N 5/04 |
| 10,902,591 | B2* | 1/2021 | Madabhushi | G06N 3/0454 |
| 2005/0165290 | A1* | 7/2005 | Kotsianti | G06T 7/0012 600/407 |
| 2006/0036372 | A1* | 2/2006 | Yener | G06V 20/695 703/11 |
| 2006/0064248 | A1* | 3/2006 | Saidi | G06V 20/695 382/128 |
| 2006/0248031 | A1* | 11/2006 | Kates | G16H 50/20 706/15 |
| 2010/0111396 | A1* | 5/2010 | Boucheron | G06K 9/6231 382/133 |
| 2010/0204973 | A1* | 8/2010 | Parkinson | G16B 50/30 703/11 |
| 2017/0262984 | A1* | 9/2017 | Barnes | G06T 7/11 |
| 2017/0329894 | A1* | 11/2017 | Kennedy | G16Z 99/00 |
| 2018/0028079 | A1 | 2/2018 | Gurevich et al. | |
| 2018/0357816 | A1* | 12/2018 | Gholap | G06V 20/69 |
| 2019/0005684 | A1* | 1/2019 | De Fauw | G06K 9/6271 |
| 2019/0156159 | A1* | 5/2019 | Kopparapu | G16H 30/40 |
| 2019/0228840 | A1* | 7/2019 | Kamens | G06T 7/0012 |
| 2019/0251688 | A1* | 8/2019 | Madabhushi | G06V 10/82 |
| 2020/0160032 | A1* | 5/2020 | Allen | G06T 7/0012 |
| 2020/0364587 | A1* | 11/2020 | Kapur | G06N 3/084 |
| 2020/0372636 | A1* | 11/2020 | Ha | G16H 30/40 |
| 2020/0388028 | A1* | 12/2020 | Agus | G06T 7/0012 |
| 2021/0132042 | A1* | 5/2021 | Do | G01N 33/57492 |
| 2021/0209753 | A1* | 7/2021 | Dogdas | G06T 7/11 |

OTHER PUBLICATIONS

Emaminejad, Nastaran, et al. "The effects of variations in parameters and algorithm choices on calculated radiomics feature values: initial investigations and comparisons to feature variability across CT image acquisition conditions." Medical Imaging 2018: Computer-Aided Diagnosis. vol. 10575. International Society for Optics and Photonics, 2018.

Komura, Daisuke, et al. "Machine learning methods for histopathological image analysis." Computational and structural biotechnology journal 16 (2018): 34-42.

Tahmassebi, Amirhessam, et al. "Impact of machine learning with multiparametric magnetic resonance imaging of the breast for early prediction of response to neoadjuvant chemotherapy and survival outcomes in breast cancer patients." Investigative radiology 54.2 (2019): 110.

* cited by examiner

SYSTEMS AND METHODS FOR PROCESSING ELECTRONIC IMAGES FOR COMPUTATIONAL ASSESSMENT OF DISEASE

RELATED APPLICATION(S)

This application claims priority to U.S. Provisional Application No. 62/957,523 filed Jan. 6, 2020, the entire disclosure of which is incorporated herein by reference in its entirety.

FIELD OF THE DISCLOSURE

Various embodiments of the present disclosure relate generally to determining the presence or absence of disease, such as cancer cells. More specifically, particular embodiments of the present disclosure relate to determining at least one of a pathological complete response (pCR) or a minimal residual disease (MRD) based on cells in a whole slide image (WSI).

BACKGROUND

Pathological complete response (pCR) may refer to the absence of residual invasive and in situ cancer cells on histology microscopy slides of resected tissue samples. pCR may be used as a surrogate endpoint to determine whether patients are responding to therapies (e.g., therapies related to breast cancer, prostate cancer, bladder cancer, colorectal cancer, etc.). For example, pCR for breast cancer may be defined as the lack of all signs of invasive cancer in the breast tissue and lymph nodes removed during surgery after treatment.

Minimal residual disease (MRD) may refer to minimal, such as submicroscopic, disease such as disease that remains occult within the patient but that may eventually lead to relapse. In cancer treatment, MRD may provide information on whether the treatment has removed the cancer or whether traces remain. Currently, pCR/MRD are determined manually via pathologists checking the tissue samples under a microscope and examining whether there are still cancer cells remaining or whether all cancer cells have been removed. This detection task may be subjective and can be challenging due to various definitions of pCR/MRD as well as treatment effects that may change the morphology of the cancerous and benign tissue due to neoadjuvant therapies. The subjectivity and level of challenge may increase when there is treatment damage.

The foregoing general description and the following detailed description are exemplary and explanatory only and are not restrictive of the disclosure. The background description provided herein is for generally presenting the context of the disclosure. Unless otherwise indicated herein, the materials described in this section are not prior art to the claims in this application and are not admitted to be prior art, or suggestions of the prior art, by inclusion in this section.

SUMMARY

According to certain aspects of the present disclosure, systems and methods are disclosed for determining cancer detection results based on digital pathology images.

A method for outputting cancer detection results includes receiving a digital image corresponding to a target specimen associated with a pathology category, wherein the digital image is an image of tissue specimen, determining a detection machine learning model, the detection machine learning model being generated by processing a plurality of training images to output a cancer qualification and further a cancer quantification if the cancer qualification is a confirmed cancer qualification, providing the digital image as an input to the detection machine learning model, receiving one of a pathological complete response (pCR) cancer qualification or a confirmed cancer quantification as an output from the detection machine learning model, and outputting the pCR cancer qualification or the confirmed cancer quantification.

A system for outputting cancer detection results includes a memory storing instructions and a processor executing the instructions to perform a process including receiving a digital image corresponding to a target specimen associated with a pathology category, wherein the digital image is an image of tissue specimen, determining a detection machine learning model, the detection machine learning model being generated by processing a plurality of training images to output a cancer qualification and further a cancer quantification if the cancer qualification is a confirmed cancer qualification, providing the digital image as an input to the detection machine learning model, receiving one of a pathological complete response (pCR) cancer qualification or a confirmed cancer quantification as an output from the detection machine learning model, and outputting the pCR cancer qualification or the confirmed cancer quantification.

A non-transitory computer-readable medium storing instructions that, when executed by processor, cause the processor to perform a method for generating a specialized machine learning model, the method includes receiving a digital image corresponding to a target specimen associated with a pathology category, wherein the digital image is an image of tissue specimen, determining a detection machine learning model, the detection machine learning model being generated by processing a plurality of training images to output a cancer qualification and further a cancer quantification if the cancer qualification is a confirmed cancer qualification, providing the digital image as an input to the detection machine learning model, receiving one of a pathological complete response (pCR) cancer qualification or a confirmed cancer quantification as an output from the detection machine learning model, and outputting the pCR cancer qualification or the confirmed cancer quantification.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DESCRIPTION OF THE EMBODIMENTS

Reference will now be made in detail to the exemplary embodiments of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a" and "an" herein do not denote a limitation of quantity, but rather denote the presence of one or more of the referenced items. In the discussion that follows, relative terms such as "about," "substantially," "approximately," etc. are used to indicate a possible variation of ±10% or less in a stated value, numeric or otherwise.

Pathology refers to the study of diseases. More specifically, pathology refers to performing tests and analysis that are used to diagnose diseases. For example, tissue samples may be placed onto slides to be viewed under a microscope by a pathologist (e.g., a physician that is an expert at analyzing tissue samples to determine whether any abnormalities exist). That is, pathology specimens may be cut into multiple sections, stained, and prepared as slides for a pathologist to examine and render a diagnosis. When uncertain of a diagnostic finding on a slide, a pathologist may order additional cut levels, stains, or other tests to gather more information from the tissue. Technician(s) may then create new slide(s) that may contain the additional information for the pathologist to use in making a diagnosis. This process of creating additional slides may be time-consuming, not only because it may involve retrieving the block of tissue, cutting it to make a new slide, and then staining the slide, but also because it may be batched for multiple orders. This may significantly delay the final diagnosis that the pathologist renders. In addition, even after the delay, there may still be no assurance that the new slide(s) will have information sufficient to render a diagnosis.

Pathologists may evaluate cancer and other disease pathology slides in for cancer detection. The present disclosure presents an automated way to identify cancer cells and to make cancer qualifications and, if applicable, cancer quantifications. In particular, the present disclosure describes various exemplary AI tools that may be integrated into the workflow to expedite and improve a pathologist's work.

For example, computers may be used to analyze an image of a tissue sample to quickly identify whether the tissue sample includes one or more cancer cells in order to determine a cancer qualification (e.g., presence or absence of cancer) as well as a cancer quantification (e.g., a degree of cancer present). Thus, the process of reviewing stained slides and tests may be conducted automatically before being reviewed by a pathologist, instead of being reviewed by a pathologist, or in conjunction with being reviewed by a pathologist. When paired with automatic slide review and cancer detection, this may provide a fully automated slide preparation and evaluation pipeline.

Such automation has, at least, the benefits of (1) minimizing an amount of time wasted by a pathologist determining the findings of a slide by manually detecting cancer cells (2) minimizing the (average total) time from specimen acquisition to diagnosis by avoiding the additional time conducting manual analysis or questionable slides, (3) reducing the amount of repeat tissue evaluation based on missed tissue areas or hard to detect tissue areas (4) reducing the cost of repeated biopsies and pathologist review by accounting for treatment effects, (5) eliminating or mitigating the need for a second or subsequent pathologist diagnostic review, (6) reducing the probability of an incorrect diagnosis, (7) increase the probability of a proper diagnosis, and/or (8) identifying or verifying correct properties (e.g., pCR, MRD, etc.) of a digital pathology image.

The process of using computers to assist pathologists is called computational pathology. Computing methods used for computational pathology may include, but are not limited to, statistical analysis, autonomous or machine learning, and AI. AI may include, but is not limited to, deep learning, neural networks, classifications, clustering, and regression algorithms. By using computational pathology, lives may be saved by helping pathologists improve their diagnostic accuracy, reliability, efficiency, and accessibility. For example, computational pathology may be used to assist with detecting slides suspicious for cancer, thereby allowing pathologists to check and confirm their initial assessments before rendering a final diagnosis.

Histopathology refers to the study of a specimen that has been placed onto a slide. For example, a digital pathology image may be comprised of a digitized image of a microscope slide containing the specimen (e.g., a smear). One method a pathologist may use to analyze an image on a slide is to identify nuclei and classify whether a nucleus is normal (e.g., benign) or abnormal (e.g., malignant). To assist pathologists in identifying and classifying nuclei, histological stains may be used to make cells visible. Many dye-based staining systems have been developed, including periodic acid-Schiff reaction, Masson's trichrome, nissl and methylene blue, and Haemotoxylin and Eosin (H&E). For medical diagnosis, H&E is a widely used dye-based method, with hematoxylin staining cell nuclei blue, eosin staining cytoplasm and extracellular matrix pink, and other tissue regions taking on variations of these colors. In many cases, however, H&E-stained histologic preparations do not provide sufficient information for a pathologist to visually identify biomarkers that can aid diagnosis or guide treatment. In this situation, techniques such as immunohistochemistry (IHC), immunofluorescence, in situ hybridization (ISH), or fluorescence in situ hybridization (FISH), may be used. IHC and immunofluorescence involve, for example, using antibodies that bind to specific antigens in tissues enabling the visual detection of cells expressing specific proteins of interest, which can reveal biomarkers that are not reliably identifiable to trained pathologists based on the analysis of H&E stained slides. ISH and FISH may be employed to assess the number of copies of genes or the abundance of specific RNA molecules, depending on the type of probes employed (e.g. DNA probes for gene copy number and RNA probes for the assessment of RNA expression). If these methods also fail to provide sufficient information to detect some biomarkers, genetic testing of the tissue may be used to confirm if a biomarker is present (e.g., overexpression of a specific protein or gene product in a tumor, amplification of a given gene in a cancer).

A digitized image may be prepared to show a stained microscope slide, which may allow a pathologist to manually view the image on a slide and estimate a number of stained abnormal cells in the image. However, this process may be time consuming and may lead to errors in identifying abnormalities because some abnormalities are difficult to detect. Computational processes using machine learning models and devices may be used to assist pathologists in detecting abnormalities that may otherwise be difficult to detect. For example, AI may be used to detect cancer cells (e.g., as they may be distinguishable from non-cancer cells) from salient regions within digital images of tissues stained using H&E and other dye-based methods. The images of the tissues could be whole slide images (WSI), images of tissue cores within microarrays or selected areas of interest within a tissue section. Using staining methods like H&E, these cancer cells may be difficult for humans to visually detect or quantify without the aid of additional testing. Using AI to detect these cancer cells from digital images of tissues has the potential to improve patient care, while also being faster and less expensive.

As described above, computational pathology processes and devices of the present disclosure may provide an integrated platform allowing a fully automated process including data ingestion, processing and viewing of digital pathology images via a web-browser or other user interface, while integrating with a laboratory information system (LIS). Further, clinical information may be aggregated using cloud-based data analysis of patient data. The data may come from hospitals, clinics, field researchers, etc., and may be analyzed by machine learning, computer vision, natural language processing, and/or statistical algorithms to do real-time monitoring and forecasting of health patterns at multiple geographic specificity levels.

Implementations of the disclosed subject matter include systems and methods for using a detection machine learning model to determine the presence or absence of cancer cells in a WSI. The detection machine learning model may be generated to determine a cancer qualification. The cancer qualification may include an indication of whether cells represented in a digital image of a tissue sample are cancer cells or if no cancer cells are identified in the digital image. According to an implementation, the cancer qualification may also include a type of cancer (e.g., breast, prostate, bladder, colorectal, etc.). If a cancer qualification is a confirmed cancer qualification, then a cancer quantification may also be output by the detection machine learning model. The cancer quantification may indicate the number, ratio, or degree of cancer cells identified from the digital image and may be a minimal residual disease (MRD) designation based on an established MRD criteria (e.g., 1 cell per million or less). If the cancer qualification output by the detection machine learning model indicates no cancer cells, a pathological complete response (pCR) cancer qualification may be output.

The detection machine learning model may be trained based on supervised, semi-supervised, weakly-supervised or un-supervised training including but not limited to multiple instance learning. Training images may be from the same pathology category as the respective digital images input to the detection machine learning model. According to an implementation, multiple different training images from a plurality of pathology categories may be used to train the detection machine learning model across pathology categories. According to this implementation, an input to the detection machine learning model may include the pathology category of the digital image. Pathology categories may include, but are not limited to, histology, cytology, frozen section, immunohistochemistry (IHC), immunofluorescence (IF), hematoxylin and eosin (H&E), hematoxylin alone, molecular pathology, 3D imaging, or the like. The detection machine learning model may be trained to detect cancer cells based on, for example, training images having tagged cancer cells. The detection machine learning model may adjust weights in one or more layers to identify regions likely to have cancer cells based on a known or determined cancer type and may further adjust weights in one or more layers based on identifying cancer cells or not finding cancer cells within those regions.

According to an implementation, a detection machine learning model may be trained using training digital images that depict tissue exhibiting treatment effects. Treatments that may result in treatment effects include, but are not limited to, neoadjuvant therapies such as hormonal therapies (androgen deprivation therapies (ADT), nonsteroidal anti-androgens (NSAA)), radiation therapy, chemotherapies, or the like. Such treatments may cause treatment damage and change the morphology of cancerous and benign cells hence making the detection based assessments more challenging than such assessments without treatment effects. Treatment effects may be a result of treatment applied to the patient from whom the tissue specimen corresponding to a digital image is obtained. Treatments can often alter the morphology of patient tissue, which is commonly known as "treatment effects," and can often make the analysis of determining cancer cells different than an analysis of tissue that does not exhibit treatment effects. The training digital images that depict tissue that exhibit treatment effects may or may not be tagged as being digital images corresponding to tissue having treatment effects. A treatment effect machine learning model may be trained based on the images that exhibit treatment effects and may be a part of the detection machine learning model. By utilizing the treatment detection machine learning model, the qualification and potential quantification of cancer by the detection machine learning model may be informed by the treatment detection machine learning model output and may provide an indication of the success or failure of a given treatment. The treatment effect machine learning model may be initialized by using a base detection machine learning model (i.e., a trained machine learning model trained based on a plurality of training images without treatment effects). Similarly, a pCR and/or MDR detection component of the detection machine learning model may be initialized by using a base detection machine learning model.

Notifications, visual indicators, and/or reports may be generated based on the output of the detection machine learning model. The reports may be based on an individual digitized image or based on a plurality of digitized images either during a given time period or generally retrospectively.

The systems disclose herein may be implemented locally (e.g., on-premises) and/or may be remote (e.g., cloud-based). The systems may or may not have user-interface(s) and workflows that pathologist(s) may directly accesses (e.g., a down-stream oncologist could be flagged based on the cancer qualification or quantification, etc.). Accordingly, implementations disclosed herein may be used as stand-alone operations, or used within a digital workflow.

While the disclosed subject matter is described as implemented based on oncology applications, they may be used for other forms of cell detection (e.g., infectious diseases cells, cystic fibrosis cells, sickle cell anemia, etc.). In addition to providing cancer detection benefits, the described implementations may be used for training health care professionals (e.g., slide technicians, pathologists, etc.) to practice cell qualification or quantification and/or diagnosis determination, while reducing the risk of patient harm.

Figure 1A:
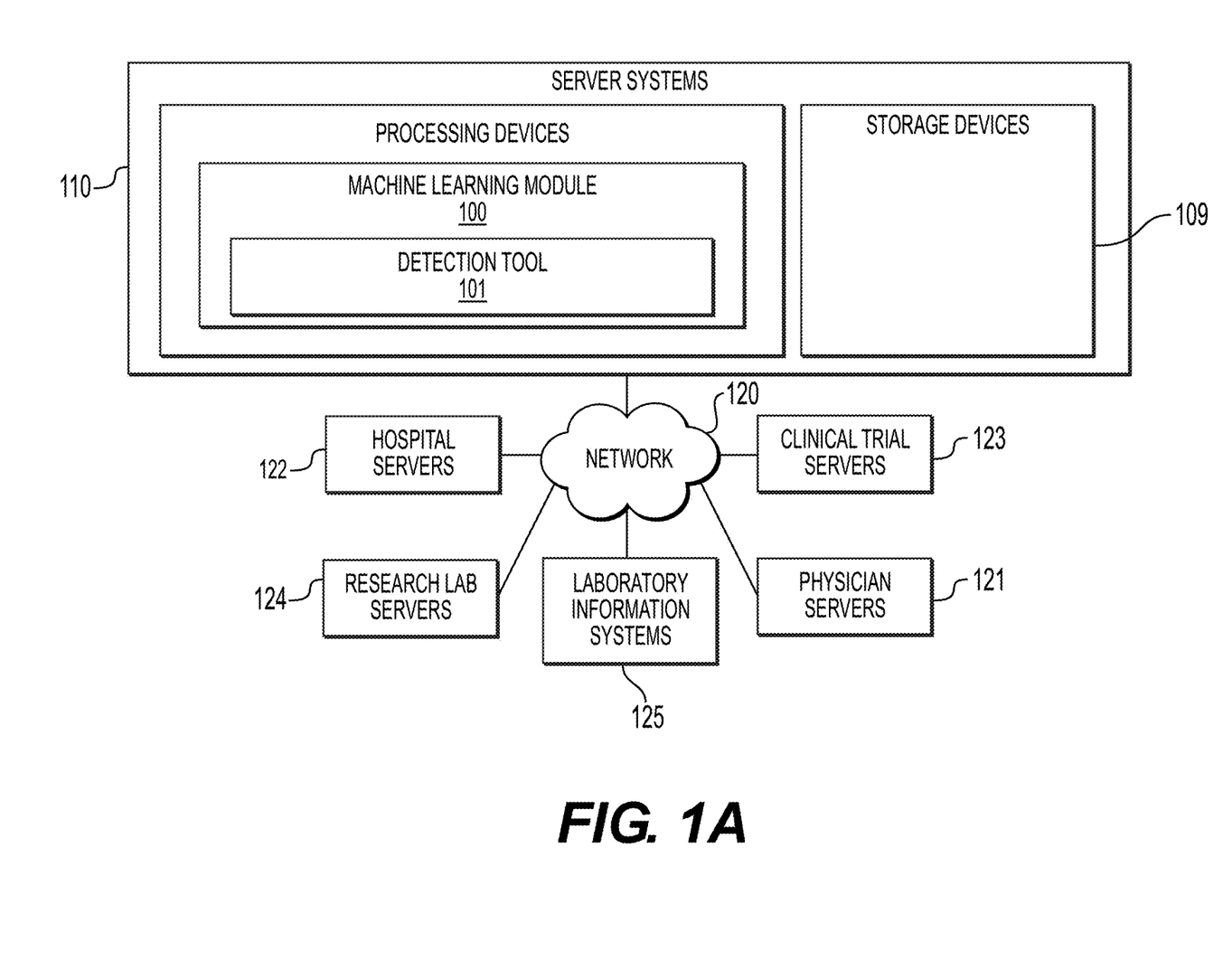
FIG. 1A illustrates an exemplary block diagram of a system and network for implementing detection tools with digital images, according to an exemplary embodiment of the present disclosure.

FIG. 1A illustrates a block diagram of a system and network for determining specimen property or image property information pertaining to digital pathology image(s), using machine learning, according to an exemplary embodiment of the present disclosure. As further disclosed herein, the system and network of FIG. 1A may include a machine learning module 100 with detection tools 101 to provide a cancer qualification output and, potentially, a cancer quantification output.

Specifically, FIG. 1A illustrates an electronic network 120 that may be connected to servers at hospitals, laboratories, and/or doctors' offices, etc. For example, physician servers 121, hospital servers 122, clinical trial servers 123, research lab servers 124, and/or laboratory information systems 125, etc., may each be connected to an electronic network 120, such as the Internet, through one or more computers, servers, and/or handheld mobile devices. According to an implementation, the electronic network 120 may also be connected to server systems 110, which may include processing devices that are configured to implement a machine learning module 100, in accordance with an exemplary embodiment of the disclosed subject matter.

The physician servers 121, hospital servers 122, clinical trial servers 123, research lab servers 124, and/or laboratory information systems 125 may create or otherwise obtain images of one or more categories of pathology specimens including patients' cytology specimen(s), histopathology specimen(s), slide(s) of the cytology specimen(s), histology, immunohistochemistry, immunofluorescence, digitized images of the slide(s) of the histopathology specimen(s), or any combination thereof. The physician servers 121, hospital servers 122, clinical trial servers 123, research lab servers 124, and/or laboratory information systems 125 may also obtain any combination of patient-specific information, such as age, medical history, cancer treatment history, family history, past biopsy or cytology information, etc. The physician servers 121, hospital servers 122, clinical trial servers 123, research lab servers 124, and/or laboratory information systems 125 may transmit digitized slide images and/or patient-specific information to server systems 110 over the electronic network 120. Server system(s) 110 may include one or more storage devices 109 for storing images and data received from at least one of the physician servers 121, hospital servers 122, clinical trial servers 123, research lab servers 124, and/or laboratory information systems 125. Server systems 110 may also include processing devices for processing images and data stored in the storage devices 109. Server systems 110 may further include one or more machine learning tool(s) or capabilities via the machine learning module 100. For example, the processing devices may include a detection tool 101, as shown as machine learning module 100, according to one embodiment. The detection tool 101 may include a detection machine learning model, as disclosed herein, as well as one or more other components such as a treatment effects machine learning model, quantification module, or the like. Alternatively or in addition, the present disclosure (or portions of the system and methods of the present disclosure) may be performed on a local processing device (e.g., a laptop).

The physician servers 121, hospital servers 122, clinical trial servers 123, research lab servers 124, and/or laboratory information systems 125 refer to systems used by pathologists for reviewing the images of the slides. In hospital settings, tissue type information may be stored in a laboratory information system 125.

Figure 1B:
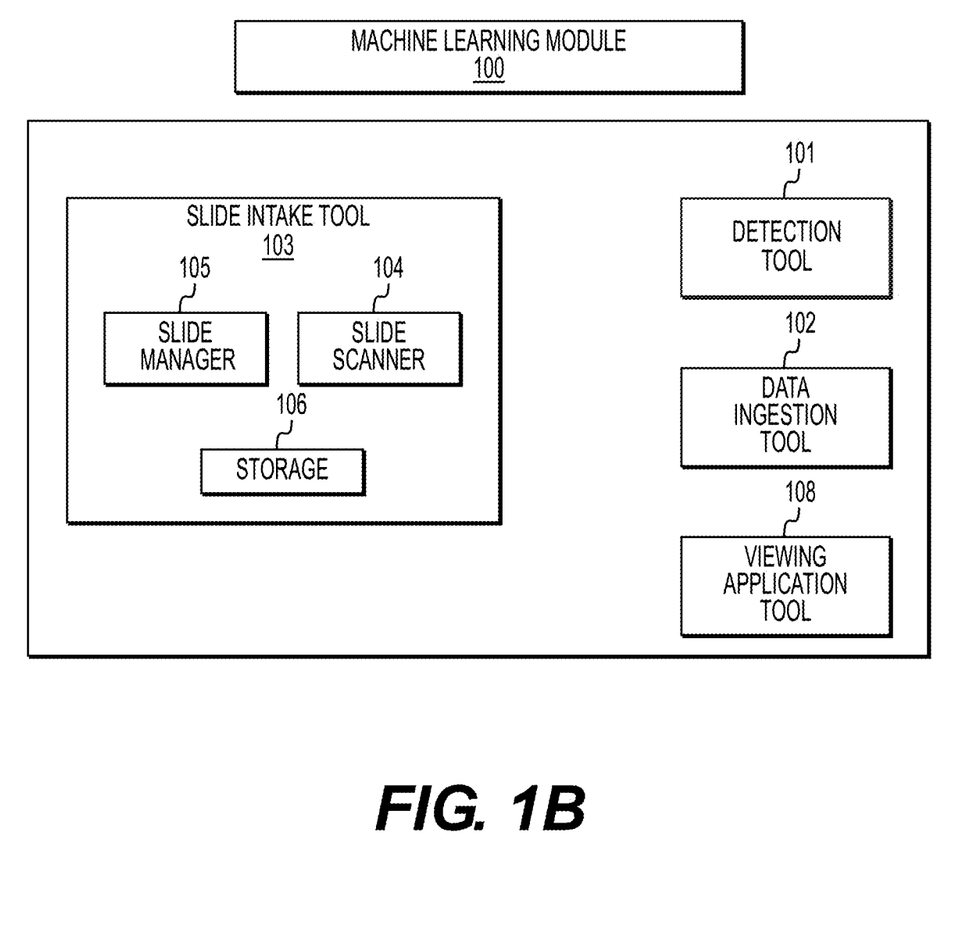
FIG. 1B illustrates an exemplary block diagram of a machine learning module, according to an exemplary embodiment of the present disclosure.

FIG. 1B illustrates an exemplary block diagram of a machine learning module 100 for determining tissue specimen property or image property information pertaining to digital pathology image(s), using machine learning.

Specifically, FIG. 1B depicts components of the machine learning module 100, according to one embodiment. For example, the machine learning module 100 may include a detection tool 101, a data ingestion tool 102, a slide intake tool 103, a slide scanner 104, a slide manager 105, a storage 106, and a viewing application tool 108. For clarification, the machine learning module 100 shown in FIGS. 1A and 1B is a previously trained and generated machine learning model (e.g., a detection machine learning model that may include a treatment effects machine learning model). Additional disclosure is provided herein for training and generating different types of machine learning models that may be used as machine learning module 100.

The detection tool 101 refers to a process and system for determining a cancer qualification, and if a confirmed cancer qualification is present, determining a cancer quantification. The cancer qualification may be a confirmed cancer qualification, a pCR cancer qualification (e.g., no cancer cells detected), or the like. A confirmed cancer qualification may indicate that one or more cancer cells were detected in the digital image of a tissue specimen. A cancer quantification may indicate the number of cancer cells detected, a ratio of cancer cells to non-cancer cells, or a degree of cancer. A subset of the cancer quantification is a MRD cancer qualification which may indicate whether the number of cancer cells are below a MRD threshold. The MRD threshold may be protocol specific, cancer type specific, institution specific, pathologist specific, or the like. The detection tool 101 may include a plurality of machine learning models or may load one machine learning model at a time. For example, the detection tool 101 may include a treatment effects machine learning model that may be trained based on a different or additional training data set then the detection machine learning model disclosed herein.

The data ingestion tool 102 refers to a process and system for facilitating a transfer of the digital pathology images to the various tools, modules, components, and devices of the machine learning module 100 that are used for characterizing and processing the digital pathology images, according to an exemplary embodiment.

The slide intake tool 103 refers to a process and system for scanning pathology images and converting them into a digital form, according to an exemplary embodiment. The slides may be scanned with slide scanner 104, and the slide manager 105 may process the images on the slides into digitized pathology images and store the digitized images in storage 106.

The viewing application tool 108 refers to a process and system for providing a user (e.g., pathologist) with a characterization or image property information pertaining to digital pathology images, according to an exemplary embodiment. The information may be provided through various output interfaces (e.g., a screen, a monitor, a storage device, and/or a web browser, etc.). As an example, the viewing application tool 108 may apply an overlay layer over a digital pathology image and the overlay layer may highlight key areas of consideration. The overlay layer may be or may be based on the output of the detection tool 101 of the machine learning module 100. As further discussed herein, the viewing application tool 108 may be used to show specific areas of a digital image that correspond to cancer cell or correspond to areas that cancer cells may be more likely.

The detection tool 101, and each of its components, may transmit and/or receive digitized slide images and/or patient information to/from server systems 110, physician servers 121, hospital servers 122, clinical trial servers 123, research lab servers 124, and/or laboratory information systems 125 over a network 120. Further, server systems 110 may include storage devices for storing images and data received from at least one of the detection tool 101, the data ingestion tool 102, the slide intake tool 103, the slide scanner 104, the slide manager 105, and viewing application tool 108. Server systems 110 may also include processing devices for processing images and data stored in the storage devices. Server systems 110 may further include one or more machine learning tool(s) or capabilities, e.g., due to the processing devices. Alternatively or in addition, the present disclosure (or portions of the system and methods of the present disclosure) may be performed on a local processing device (e.g., a laptop).

The detection tool 101 may provide the output of the machine learning module 100 (e.g., a cancer qualification, cancer quantification, pCR qualification, MRD qualification, etc.). As an example, the slide intake tool 103 and the data ingestion tool 102 may receive inputs to the machine learning module 100 and the detection tool 101 may identify cancer cells in the slides based on the data, and output an image highlighting the cancer cells or associated areas via the viewing application tool 108.

Any of the above devices, tools, and modules may be located on a device that may be connected to an electronic network 120, such as the Internet or a cloud service provider, through one or more computers, servers, and/or handheld mobile devices.

Figure 2:
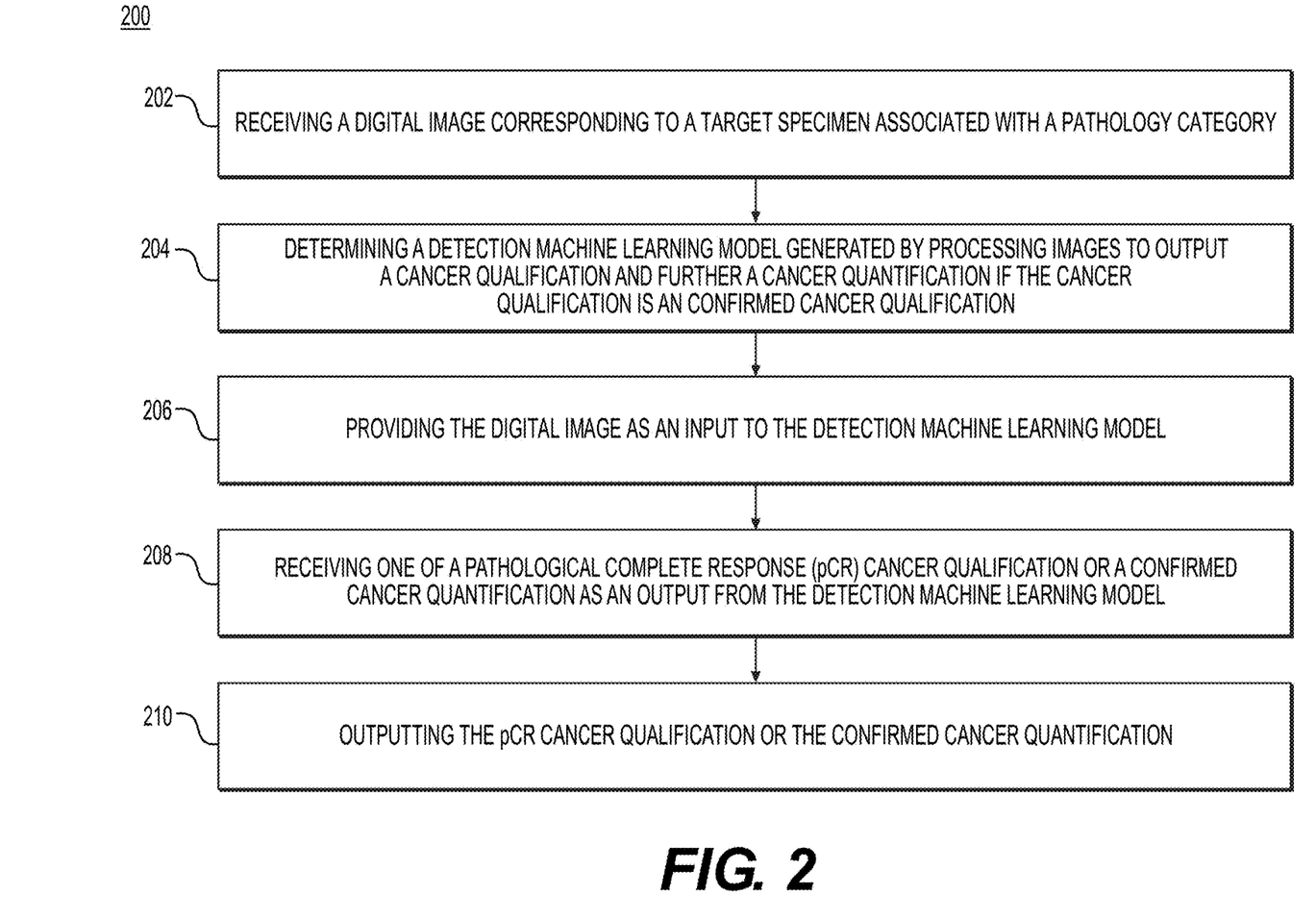
FIG. 2 is a flowchart illustrating an exemplary method for using a detection machine learning model, according to an exemplary embodiment of the present disclosure.

FIG. 2 shows a flowchart 200 for outputting cancer qualifications and quantifications based on digital images, in accordance with exemplary implementations of the disclosed subject matter. At 202 of FIG. 2, a digital image corresponding to a target specimen associated with a pathology category may be received. The digital image may be a digital pathology image captured using the slide intake tool 103 of FIG. 1B. At 204, a detection machine learning model may be determined (e.g., at the machine learning module 100). The detection machine learning model may be trained by processing a plurality of training images that are from the same pathology category as the digital image received at 202. The pathology categories may include, but are not limited to histology, cytology, frozen section, or immunohistochemistry. According to an implementation, the detection machine learning model may be trained using training images from a plurality of different pathology categories. A digital image corresponding to a target specimen, as received at 202, may also be received along with its pathology category which may be provided as an input to the detection machine learning model. At 206, the digital image from 202 may be provided to the detection machine learning model as an input to the model. One or more other attributes may also be provided as an input to the detection machine learning model. The one or more other attributes may include, but are not limited to, a pathology category, a slide type, a glass type, a tissue type, a tissue region, a chemical used, a stain amount, time applied, scanner type, date, or the like. At 208, the detection machine learning model may output a cancer qualification (e.g., a pCR cancer qualification) or a confirmed cancer quantification (e.g., an amount of cancer). According to an implementation, a confirmed cancer qualification (e.g., presence of cancer) may be received in addition to or instead of a confirmed cancer quantification. The cancer qualification may determine if a cancer quantification is generated. For example, if a confirmed cancer qualification indicates the presence of cancer cells then a cancer quantification (e.g., a number of cancer cells) may be determined. A qualification indicating a lack of cancer cells may not require a cancer quantification unless the cancer qualification threshold is greater than zero cancer cells. At 210, the cancer qualification (e.g., pCR cancer qualification, confirmed cancer qualification, etc.) and, if applicable, a cancer quantification may be output as a data signal, a report, a notification, an alert, a visual output (e.g., via viewing application tool 108), or the like.

Traditional techniques for detecting cancer cells such as via a manual pathologist review can be subjective and challenging due to the complexity of tissue, various attributes of qualification and quantification (e.g., pCR/MRD), definitions of pCR/MRD, and/or treatment effects that may change the morphology of cancerous and benign tissue due to, for example, neoadjuvant therapies. The techniques and systems based on the process described in flowchart 200 of FIG. 2 enable robust, objective, and more accurate computational assessment of cancer qualification or quantification including pCR and MRD. MRD and pCR designation may be used as a surrogate endpoint for assessment of disease-free survival and overall survival to accelerate clinical trials (e.g., for breast cancer). The automated nature of the process described in FIG. 2 may expedite results and/or treatment approval.

As shown in FIG. 2, a digital image corresponding to a target specimen associated with a pathology category may be received at 202. The target specimen may be a biopsied or otherwise retrieved tissue sample retrieved from a patient. The target specimen may be retrieved during a surgical procedure where a portion of a patient's tissue is retrieved from the patient's body for analysis. The target specimen may be a portion or subset of the total amount of tissue extracted from the patients such that multiple specimen slides may be generated from the tissue extracted from a single procedure.

The target specimen may be associated with at least one pathology category or technique such as histology, cytology, frozen section, H&E, Hematoxylin alone, IHC, molecular pathology, 3D imaging, or the like, as disclosed herein. According to an implementation, the pathology category and other image information about the digital image or target specimen may also be received. The image information may include, but is not limited to a slide type, a glass type, a tissue type, a tissue region, a chemical used, and a stain amount.

At 204, a detection machine learning model may be determined. The detection machine learning model may be trained and generated at the machine learning module 100 or may be trained and generated externally and be received at the machine learning module 100. The detection machine learning model may be trained by processing a plurality of training images at least some of which are from the same pathology category as the digital image received at 202. The pathology categories may include, but are not limited to, histology, cytology, frozen section, H&E, Hematoxylin alone, IHC, molecular pathology, 3D imaging, or the like. The detection machine learning model may be instantiated using one or more of deep learning, including but not limited to Deep Neural Networks (DNN), Convolutional Neural Networks (CNN), Fully Convolutional Networks (FCN) and Recurrent Neural Networks (RCN), probabilistic models, including but not limited to Bayesian Networks and Graphical Models, and/or discriminative Models, including but not limited to Decision Forests and maximum margin methods, or the like. These models may be trained in supervised, semi-supervised, weakly-supervised or un-supervised fashion such as using multiple instance learning. A quantification component of the detection machine learning model or separate machine learning model may also use machine learning techniques do generate outputs for quantification of cancer within a digital image (e.g., number of cancer cells within the image). A quantification component may be trained using, but not limited to, deep learning, CNNs, multiple instance learning, or the like or a combination thereof.

The detection machine learning model may be trained to output cancer qualifications and quantifications, as disclosed herein. Cancer qualifications may be output for one or more of a plurality of different cancer types. The detection machine learning model may be trained using images from the one or more of the plurality of different cancer types. For example, the training images may include images related to breast cancer, prostate cancer, and lung cancer. Accordingly, the generated detection machine learning model may receive a digital image at 202 of FIG. 2 and may qualify the image as representing tissue that includes cancer cells, the number of cancer cells, and/or the type of cancer cells. The detection machine learning model may output the cancer qualification and/or quantification based on weights and/or layers trained during its training process. Based on the weights and/or layers, the detection machine learning model may identify regions of a digital image that may more strongly be used as evidence for the presence or absence of cancer and, further, the extent of the cancer. The model may then evaluate some or all of those regions to determine the presence, absence, and/or extent of cancer cells based on training with images that provide the same. Feedback (e.g., pathologist confirmation, correction, adjustment, etc.) may further train the detection machine learning model during operation of the model.

To generate the detection machine learning model at 204, a training dataset including a large plurality of digital pathology images of pathology specimens (e.g., histology, cytology, frozen section, H&E, Hematoxylin alone, IHC, molecular pathology, 3D imaging, etc.) may be applied. The digital pathology images may be digital images generated based on physical biopsy samples, as disclosed herein, or may be images that are algorithmically generated to replicate tissue specimen (e.g., human, animal, etc.) by, for example, a rendering system or a generative adversarial model. Image or specimen associated information (e.g., slide type, a glass type, a tissue type, a tissue region, a chemical used, a stain amount, time applied, scanner type, date, etc.) may also be received as part of the training dataset. Additionally, as part of training the detection machine learning model, each image may be paired with output information about the known or assumed cancer qualification and, if applicable, cancer quantification. Such output information may include an indication of cancer presence or absence, type of cancer, and/or extent of cancer. The detection machine learning model may learn from a plurality of such training images and associated information such that the detection machine learning model is trained by modifying one or more weights based on the qualifications and quantifications associated with each training image. Although a supervised training is provided as an example, it will be understood that the training of the detection machine learning model may be in supervised, semi-supervised, weakly-supervised or un-supervised.

The training dataset including the digital pathology images, the image or specimen associated information, and/or the output information may be generated and/or provided by one or more of the systems 110, physician servers 121, hospital servers 122, clinical trial servers 123, research lab servers 124, and/or laboratory information systems 125. Images used for training may come from real sources (e.g., humans, animals, etc.) or may come from synthetic sources (e.g., graphics rendering engines, 3D models, etc.). Examples of digital pathology images may include (a) digitized slides stained with a variety of stains, such as, but not limited to, H&E, Hematoxylin alone, IHC, molecular pathology, etc., and/or (b) digitized tissue samples from a 3D imaging device, such as microCT.

The detection machine learning model may be generated based on applying the digital pathology images with, optionally, the associated information paired with the output information as applied by a machine learning algorithm. The machine learning algorithm may accept, as inputs, the pathology specimens, the associated information, and the output information (e.g., cancer qualifications, cancer quantifications, etc.) and implement training using one or more techniques. For example, the detection machine learning model may be trained in one or more deep learning algorithms such as, but not limited to, DNN, CNN, FCN, RCN, CNN with multiple-instance learning or multi-label multiple instance learning, Recurrent Neural Networks (RNN), Long-short term memory RNN (LSTM), Gated Recurrent Unit RNN (GRU), graph convolution networks, or the like or a combination thereof. Convolutional neural networks can directly learn the image feature representations necessary for discriminating among characteristics, which can work extremely well when there are large amounts of data to train on for each specimen, whereas the other methods can be used with either traditional computer vision features, e.g., SURF or SIFT, or with learned embeddings (e.g., descriptors) produced by a trained convolutional neural network, which can yield advantages when there are only small amounts of data to train. The trained detection machine learning model may be configured to provide cancer qualification and/or cancer quantification outputs based on the digital pathology images.

Figure 3:
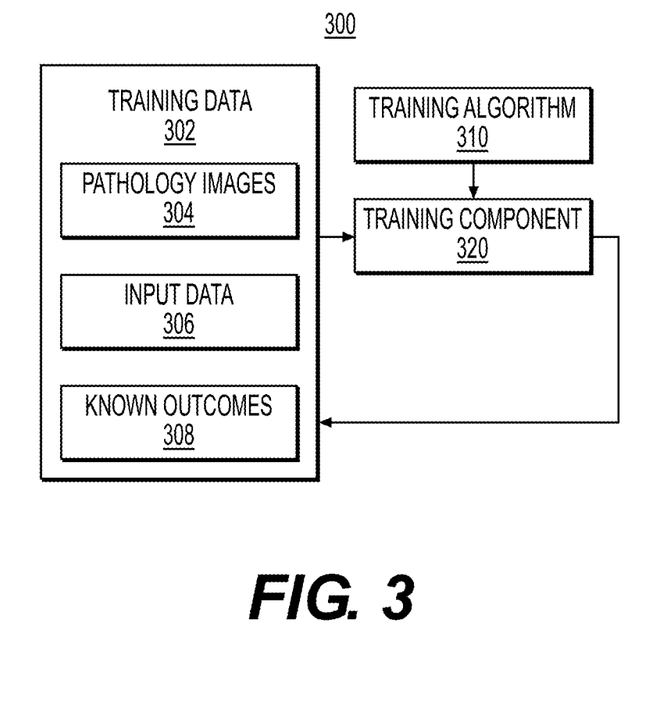
FIG. 3 illustrates an exemplary block diagram of a training module, according to an exemplary embodiment of the present disclosure.

FIG. 3 shows an example training module 300 to train a detection machine learning model. As shown in FIG. 3, training data 302 may include one or more of pathology images 304 (e.g., digital representation of biopsied images), input data 306 (e.g., cancer type, pathology category, etc.), and known outcomes 308 (e.g., quality designations) related to the pathology images 304. The training data 302 and a training algorithm 310 may be provided to a training component 320 that may apply the training data 302 to the training algorithm 310 in order to generate a detection machine learning model.

At 206, the detection machine learning model may be provided an input including a patient based digital pathology image (e.g., a digital image of pathology specimen (e.g., histology, cytology, immunohistochemistry etc.)) as well as, optionally, associated information. The detection machine learning model's internal weights and/or layers may be applied to the digital pathology image and the associated information to determine a cancer qualification and, if applicable, a cancer quantification.

A cancer qualification may be a presence or absence of cancer. The cancer qualification may be a binary determination such detecting a single cancer cell may correspond to a cancer presence and not detecting a single cancer cell may correspond to an absence of cancer. A pCR cancer qualification may correspond to an absence of cancer and may be output when no cancer cells are detected.

According to an implementation, the cancer presence and/or pCR cancer qualification may be protocol specific such that the protocol may define one or more thresholds for cancer qualification. As an example, a protocol may dictate that a minimum of five cancer cells per million cells is required to output presence of cancer and less than five cancer cells per million is sufficient for a pCR cancer qualification.

Additionally, as disclosed herein, the detection machine learning model may be configured to output a cancer type based on the image data received as input. The cancer type output may be a determined cancer type or an indication of a probability of the cancer type. The cancer type output may be informed by inputs in addition to a tissue specimen based digital image and may include tissue characteristics, slide type, glass type, tissue type, tissue region, chemical used, and/or stain amount.

A cancer quantification may be output when the presence of cancer is detected. The cancer quantification may include a number of cancer cells (e.g., a number of cancer cells per million), density of cancer cells, or may be an indication that the number of cancer cells is above a threshold amount (e.g., an MRD threshold). For example, the cancer quantification may be or may include a MRD cancer quantification that may refer to submicroscopic disease such as disease that remains occult within the patient but that may eventually lead to relapse. In cancer treatment, MRD may provide information on whether the treatment has removed the cancer or whether traces remain.

The output of the detection machine learning model (i.e., the cancer qualification and, if applicable, cancer quantification), at 210, may be provided to a storage device 109 of FIG. 1A (e.g., cloud storage, hard drive, network drive, etc.). The output of the detection machine learning model may be or may also be a notification based on the cancer qualification or cancer quantification. The notification may include information about the cancer qualification, cancer quantification, cancer type, location of cancer cells, or the like. The notification may be provided via any applicable technique such as a notification signal, a report, a message via an application, a notification via a device, or the like. The notification may be provided to any applicable device or personnel (e.g., histology technician, scanner operator, pathologist, record, etc.). As an example, the output of the detection machine learning model may be integrated with corresponding target specimen's history in, for example, the laboratory information systems 125 that stores a record of the patient and the associated target specimen.

According to an implementation, the output of the detection machine learning model may be a report based on the cancer qualification, cancer quantification, cancer type, location of cancer cells, a change over time in any such factors, or the like. The report may be in any applicable format such as a PDF format, HTML format, in-app format, or the like.

According to an implementation, the output of the detection machine learning model, at 210, may be or may include a visual indicator. The visual indicator may be provided, for example, via the viewing application tool 108 of FIG. 1B. The visual indicator may provide a visual representation of the digital image and may provide indications regarding the cells used when determining the cancer qualification or cancer quantification.

Figure 4:
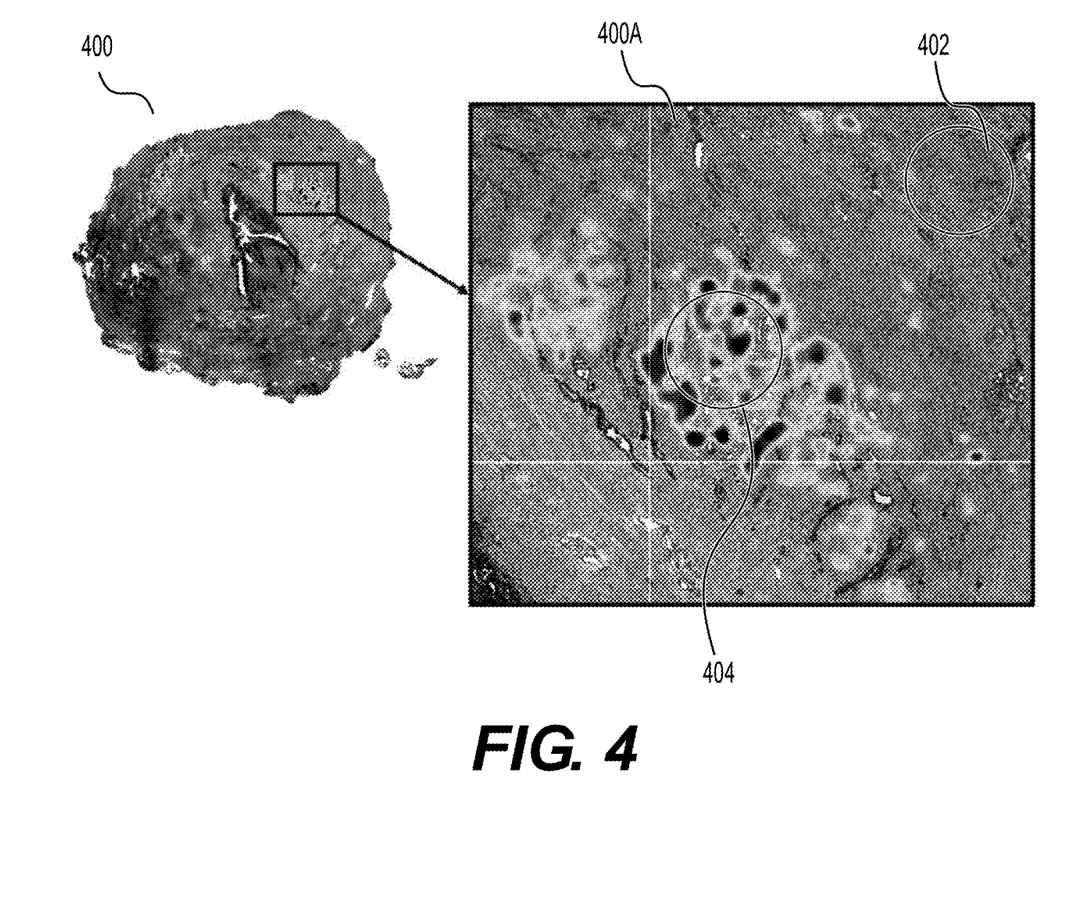
FIG. 4 illustrates a diagram for detecting cancer cells using a detection module, according to an exemplary embodiment of the present disclosure.

FIG. 4 shows an example, digital image 400 which is expanded to provide an expanded view 400A. The digital image 400 of FIG. 4 is an H&E slide with treatment effects due to hormonal therapy for prostate cancer. As shown in the expanded view 400A, an area of cells that is not relied upon to make a cancer qualification and/or cancer quantification is shown at area 402. Area 402 may correspond to an area that the detection machine learning model determined as less relevant for detection purposes. Area 402 corresponds to an area that the detection machine learning model determines as a benign tissue region with no cancer cells detected. An area of cells that is relied upon to make a cancer qualification and/or cancer quantification is shown at area 404. As compared to the digital image 400 of a tissue specimen, the area 404 relied upon to make cancer qualification and/or cancer quantification may be relatively small. Area 404 may correspond to an area that the detection machine learning model determined as more relevant for detection purposes. Area 404 corresponds to an area that the detection machine learning model determines as a cancerous tissue region with at least one cancer cell detected.

According to an implementation, the detection machine learning algorithm may also be trained based on and/or receive as inputs clinical information (e.g. patient information, surgical information, diagnostic information, etc.), laboratory information (e.g. processing times, personnel, tests, etc.). The detection machine learning algorithm may provide cancer qualification and/or cancer quantification based on such inputs.

According to an implementation, the detection machine learning model may include a treatment effect machine learning model, as disclosed herein. Treatment effects may correspond to oncology treatments based in medicinal drugs, hormonal therapy, chemotherapy, etc.). Tissue samples from patients treated using a therapy (e.g., cancer therapy) may have properties that are different than tissues samples from patients that have not been treated using similar therapies.

The treatment effect machine learning model may be generated using a low shot or transfer learning method and may be initialized by using a base detection machine learning model (i.e., a trained machine learning model trained based on a plurality of training images excluding treatment effects). For example, a sample detection machine learning model as disclosed herein may be trained using digital images from tissue samples from patients that have not undergone treatment and/or whose tissue samples do not exhibit treatment effects. The treatment machine learning model may be initialized using the sample detection machine learning model such that, weights and/or one or more layers associated with the sample detection machine learning model are kept and additional weights, weight modifications, layers, and/or layer modifications are applied when generating the treatment effect machine learning model. Similarly, a pCR and/or MDR detection component of the detection machine learning model may be initialized by using a base detection machine learning model.

Figure 5:
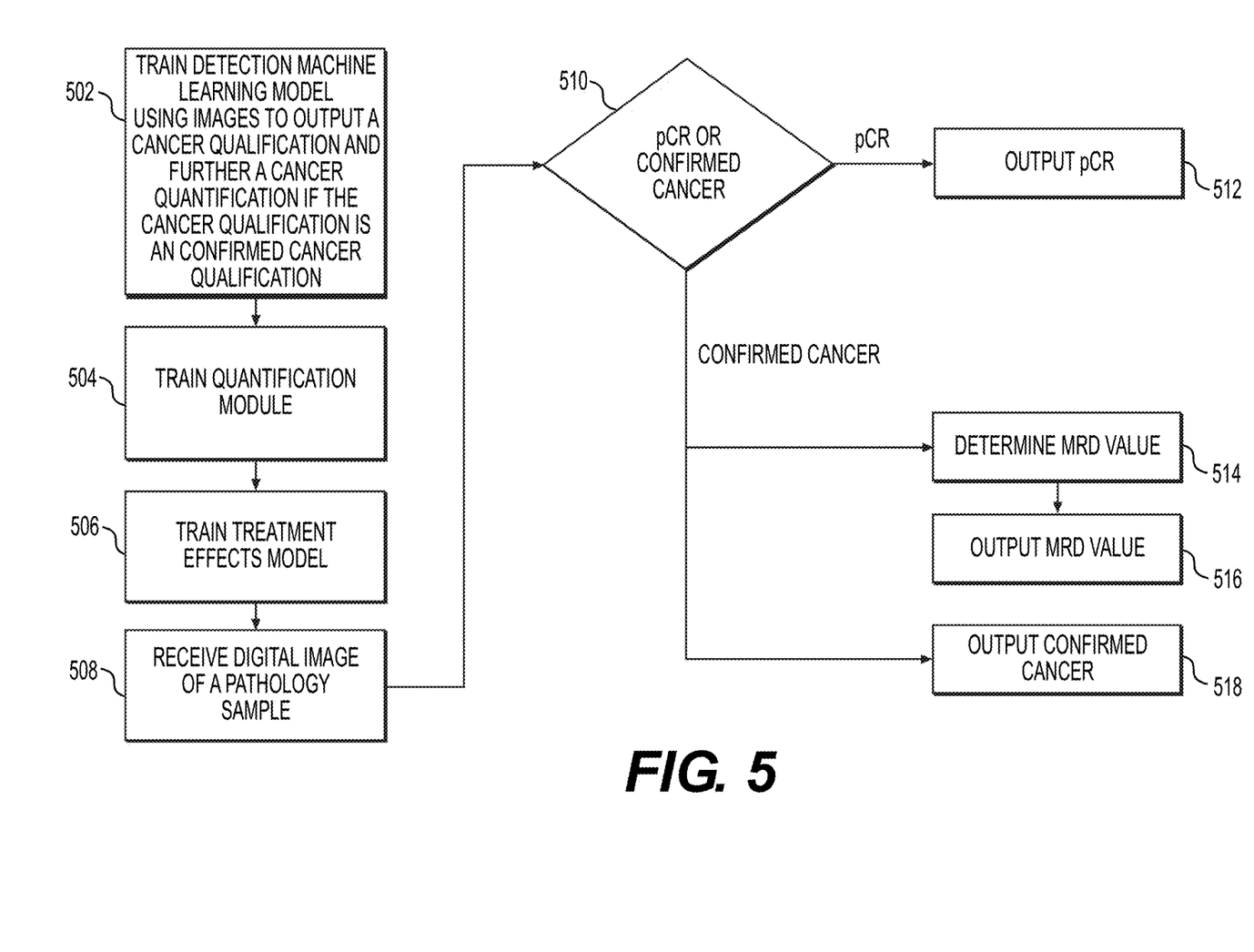
FIG. 5 is a flowchart of an exemplary embodiment of a detection implementation, according to an exemplary embodiment of the present disclosure.

FIG. 5 shows an example implementation of the detection analysis as disclosed herein in reference to FIG. 2. FIG. 5 shows a flowchart for a process of predicting pCR and/or MRD in prostate cancer with treatment effects. In the example of prostate cancer, pCR and MRD may be used as endpoints for clinical trials that assess neoadjuvant treatments. However, a major challenge is the presence of treatment effects in assessing cancer.

At 502, a detection machine learning model may be trained using images to output a cancer qualification and, if applicable a cancer quantification if the cancer qualification is a confirmed cancer qualification. The training may include inputting one or more digital images of prostate tissue (e.g., histopathology, H&E, IHC, 3D imaging, etc.), including an indication of the presence or absence of cancer. The detection training model may be trained using one or more machine learning algorithms and/or formats, as disclosed herein (e.g., deep learning, DNN, CNN, FCN, RCN, probabilistic models, discriminative models, etc.). The detection learning model may be trained to output the cancer qualification, cancer qualification, as well as an assessment of pCR and/or MRD which may be protocol specific, as disclosed herein. The training images may include images that may be or may be tagged as being one of pCR or MRD.

At 504, a quantification module may be trained based on the digital images applied at 502. To train the quantification module, a quantification of the amount of prostate cancer (e.g., a number of cells exhibiting prostate cancer) may be included with all or a subset of the digital images used to train the model. It will be understood that the quantification module may be part of the overall detection model trained at 502.

At 506, a treatment effects module may be trained based on the digital images applied at 502. All or a subset of the digital images applied at 502 may depict tissue exhibiting treatment effects. The treatment effects may be inherent in the images or may be tagged such that the tags are used as part of the training.

At 508, a digital image of a pathology sample may be received as an input to the trained detection machine learning model of 502 as well as one or more of the quantification module of 504 and treatment effects module of 506.

At 510, the detection machine learning model of 502, quantification module of 504, and/or treatment effects module of 506 may be used to determine a pCR cancer qualification a confirmed cancer qualification. If a pCR cancer qualification is determined, the pCR cancer qualification may be output (e.g., via a notification, report, visual indication, etc.) at 512. If a confirmed cancer qualification is determined, the confirmed cancer qualification may be output at 518. Additionally, or alternatively, a cancer quantification may be determined. For example, an MRD value may be determined at 514 and may be output at 516.

Figure 6:
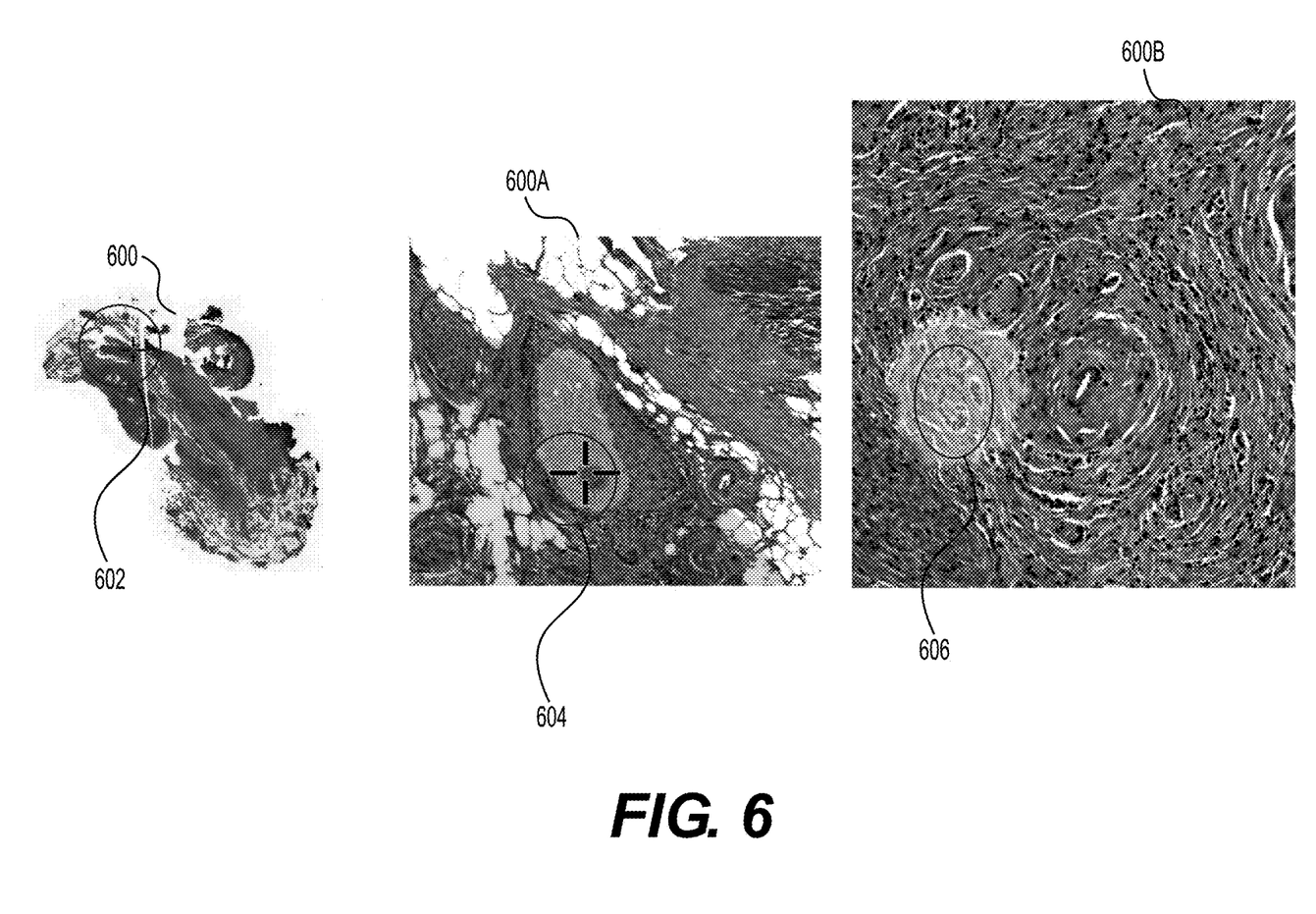
FIG. 6 is a diagram of an experimental result of using a detection model, according to an exemplary embodiment of the present disclosure.

FIG. 6 shows an experimental based on the process disclosed in flowchart 200 of FIG. 2. FIG. 6 is related to the pathological evaluation of prostate cancer treated with neoadjuvant hormonal treatment in radical prostatectomy whole mount sections. Such an evaluation traditionally poses a significant challenge because of morphologic changes of the tumor combined with the possibility of very small foci of residual tumor in a large volume of non-neoplastic tissue.

A detection machine learning model applied for this experiment may utilize a multiple instance learning approach to train a whole-slide image classifier using an SE-ResNet50 convolutional neural network. The model, in this example, was trained on 36,644 WSIs (7,514 had cancerous foci), with a reduced embedding size to accommodate the extremely large number of patch instances in a whole mount slide. The detection machine learning model was then fine-tuned in a fully-supervised context on a small annotated set of radical prostatectomy specimens retrieved from prostate cancer patients treated in the neoadjuvant setting to further improve performance on radical prostatectomy data. This produced an AUC of 0.99 on anti-androgen treated cases.

The detection machine learning model showed an AUC of 0.99 in cases with anti-androgen receptor neoadjuvant therapy. After training, this example system was evaluated on 40 WSI images of H&E stained whole mount prostatectomy slides from 15 prostatectomy specimens retrieved from patients after neoadjuvant treatment with anti-androgen therapy. Ground truth was established by pathologist annotations. All 37 malignant WSIs (three WSIs contained tumor <5 mm, 34 WSIs contained tumor >5 mm) were correctly classified as harboring treated cancer by the system. Of the three benign WSIs, the detection machine learning model incorrectly classified one benign lesion as cancer, while the other two were correctly classified as benign tissue.

Accordingly, accurate slide level classification of H&E stained slides from radical prostatectomy specimens has the potential to improve accuracy and efficiency of histopathologic evaluation of whole mount sections from radical prostatectomy specimens of patients who have received neoadjuvant treatment prior to surgery. As shown in FIG. 6, a digital image 600 includes a visual indication of cells that are relied upon in area 602. An enlarged view 600A shows a specific area 604 within the area 602 that more clearly shows the cells relied upon by the detection machine learning model and also shows cancer cells within area 604. A further enlarged view 600B shows a specific area 606 within specific area 604 that even more clearly shows the cells relied upon by the detection machine learning model and also shows cancer cells and/or benign cells within the area 606.

Figure 7:
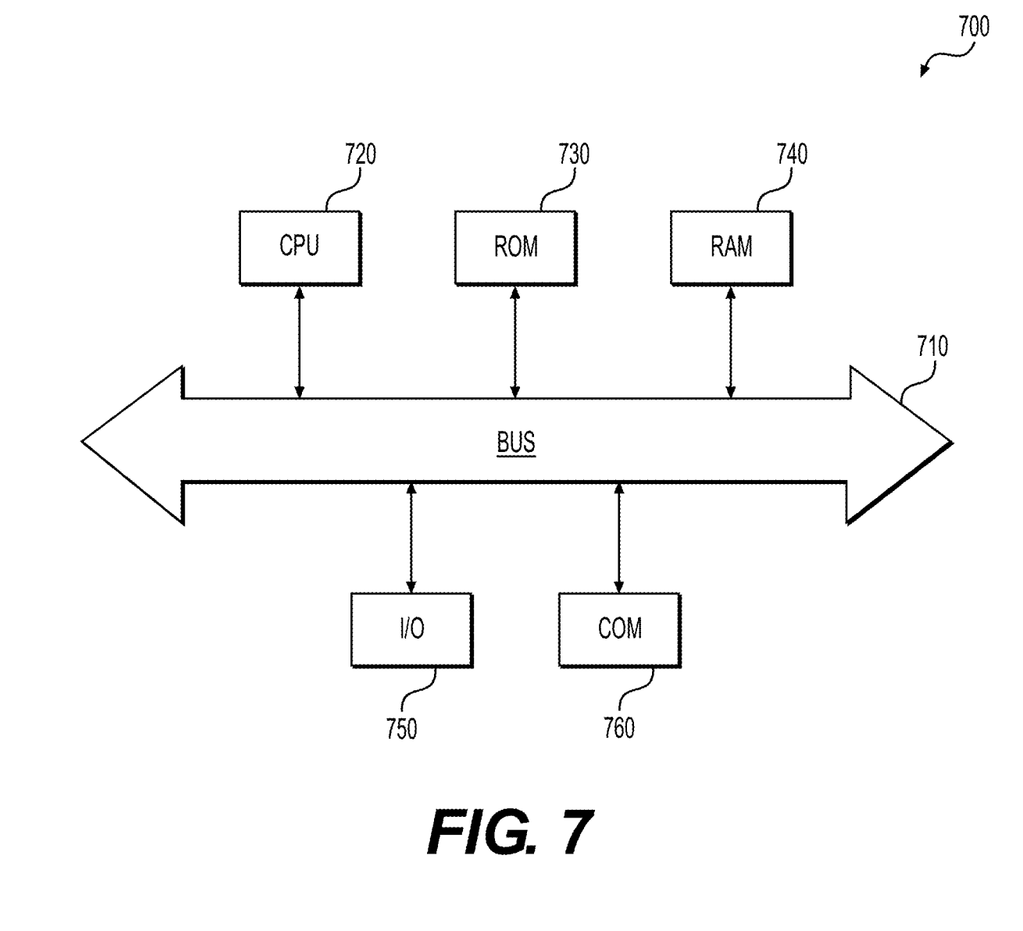
FIG. 7 depicts an example system that may execute techniques presented herein.

Device 700, of FIG. 7, may correspond to hardware utilized by server systems 110, hospital servers 122, research lab servers 124, clinical trial servers 123, physician servers 121, laboratory information systems 125, and/or client devices, etc. Device 700 may include a central processing unit (CPU) 720. CPU 720 may be any type of processor device including, for example, any type of special purpose or a general-purpose microprocessor device. As will be appreciated by persons skilled in the relevant art, CPU 720 also may be a single processor in a multi-core/multiprocessor system, such system operating alone, or in a cluster of computing devices operating in a cluster or server farm. CPU 720 may be connected to a data communication infrastructure 710, for example, a bus, message queue, network, or multi-core message-passing scheme.

Device 700 also may include a main memory 740, for example, random access memory (RAM), and may include a secondary memory 730. Secondary memory 730, e.g., a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage unit may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 730 may include other similar means for allowing computer programs or other instructions to be loaded into device 700. Examples of such means may include a program cartridge and cartridge interface (such as that found in video game devices), a removable memory chip (such as an EPROM, or PROM) and associated socket, and other removable storage units and interfaces, which allow software and data to be transferred from a removable storage unit to device 700.

Device 700 also may include a communications interface ("COM") 760. Communications interface 760 allows software and data to be transferred between device 700 and external devices. Communications interface 760 may include a modem, a network interface (such as an Ethernet card), a communications port, a PCMCIA slot and card, or the like. Software and data transferred via communications interface 760 may be in the form of signals, which may be electronic, electromagnetic, optical, or other signals capable of being received by communications interface 760. These signals may be provided to communications interface 760 via a communications path of device 700, which may be implemented using, for example, wire or cable, fiber optics, a phone line, a cellular phone link, an RF link or other communications channels.

The hardware elements, operating systems and programming languages of such equipment are conventional in nature, and it is presumed that those skilled in the art are adequately familiar therewith. Device 700 also may include input and output ports 750 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Throughout this disclosure, references to components or modules generally refer to items that logically can be grouped together to perform a function or group of related functions. Like reference numerals are generally intended to refer to the same or similar components. Components and modules can be implemented in software, hardware, or a combination of software and hardware.

The tools, modules, and functions described above may be performed by one or more processors. "Storage" type media may include any or all of the tangible memory of the computers, processors or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution.

The foregoing general description is exemplary and explanatory only, and not restrictive of the disclosure. Other embodiments of the invention will be apparent to those skilled in the art from consideration of the specification and practice of the invention disclosed herein. It is intended that the specification and examples be considered as exemplary only.

What is claimed is:

1. A computer-implemented method for processing electronic images, the method comprising:
    receiving a digital image corresponding to a target specimen collected using a histopathology technique, wherein the digital image is an image of tissue specimen;
    determining a detection machine learning model, the detection machine learning model being generated by processing a plurality of training images to output a cancer qualification and further output a cancer quantification if the cancer qualification is an confirmed cancer qualification;
    providing the digital image as an input to the detection machine learning model;
    receiving a pathological complete response (pCR) cancer qualification when the output of the detection machine learning model comprises a pCR cancer qualification and receiving a confirmed cancer quantification comprising one of a number of cancer cells or a density of cancer cells when the output of the detection machine learning model comprises a confirmed cancer quantification, and wherein receiving the confirmed cancer quantification also comprises receiving a type of cancer when the output of the detection machine learning model comprises a confirmed cancer quantification, wherein the type of cancer is determined based on the digital image and one or more of a tissue characteristics, slide type, glass type, tissue type, tissue region, chemical used, or stain amount, wherein the detection machine learning model comprises a treatment effect machine learning model, and wherein the treatment effect machine learning model is initialized with one of weights and/or layers from a trained version of the detection machine learning model and the treatment effect machine learning model is trained based on tagged treatment effects in the plurality of training images; and
    outputting the pCR cancer qualification or the confirmed cancer quantification based on the treatment effects machine learning model.

2. The computer-implemented method of claim 1, wherein receiving the confirmed cancer quantification comprises receiving a minimal residual disease (MRD) cancer quantification.

3. The computer-implemented method of claim 2, wherein the MRD cancer quantification is protocol specific.

4. The computer-implemented method of claim 2, wherein the MRD cancer quantification corresponds to a number of cancer cells below a MRD threshold.

5. The computer-implemented method of claim 1, wherein the pCR cancer qualification corresponds to the digital image having zero detectable cancer cells.

6. The computer-implemented method of claim 1, wherein the plurality of training images comprise images with treatment effects.

7. A system for processing electronic images, the system comprising:
    at least one memory storing instructions; and
    at least one processor executing the instructions to perform operations comprising:

receiving a digital image corresponding to a target specimen collected using a histopathology technique, wherein the digital image is an image of tissue specimen;

determining a detection machine learning model, the detection machine learning model being generated by processing a plurality of training images to output a cancer qualification and further output a cancer quantification if the cancer qualification is a confirmed cancer qualification;

receiving tagged treatment effects in the plurality of training images;

providing the digital image as an input to the detection machine learning model wherein the processor is configured to receive a pathological complete response (pCR) cancer qualification when the output of the detection machine learning model comprises the pCR cancer qualification and also configured to receive a confirmed cancer quantification comprising one of a number of cancer cells or a density of cancer cells when the output of the detection machine learning model comprises the confirmed cancer quantification, and wherein receiving the confirmed cancer quantification also comprises receiving a type of cancer when the output of the detection machine learning model comprises a confirmed cancer quantification, wherein the type of cancer is determined based on the digital image and one or more of a tissue characteristics, slide type, glass type, tissue type, tissue region, chemical used, or stain amount;

receiving the pCR cancer qualification when the output of the detection machine learning model comprises the pCR qualification and receiving the confirmed cancer qualification when the output of the detection machine learning model comprises the confirmed cancer qualification, wherein the detection machine learning model comprises a treatment effect machine learning model, and wherein the treatment effect machine learning model is initialized with one of weights or layers from a trained version of the detection machine learning model and the treatment effect machine learning model is trained based on tagged treatment effects in the plurality of training images; and outputting the pCR cancer qualification or the confirmed cancer quantification based on the treatment effects machine learning model.

8. The system of claim 7, wherein receiving the confirmed cancer qualification further comprises receiving a minimal residual disease (MRD) cancer quantification.

9. The system of claim 8, wherein the MRD cancer qualification is protocol specific.

10. The system of claim 7, wherein the confirmed cancer qualification corresponds to detecting a threshold number of cancer cells.

11. The system of claim 7, wherein the plurality of training images comprise images with treatment effects.

12. The system of claim 7, wherein the detection machine learning model comprises a treatment effect machine learning model.

13. A non-transitory computer-readable medium storing instructions that, when executed by processor, cause the processor to perform operations for processing electronic images, the operations comprising:

receiving a digital image corresponding to a target specimen collected using a histopathology technique, wherein the digital image is an image of tissue specimen;

determining a detection machine learning model, the detection machine learning model being generated by processing a plurality of training images to output a cancer qualification and further output a cancer quantification if the cancer qualification is a confirmed cancer qualification;

providing the digital image as an input to the detection machine learning model wherein the processor is configured to receive a pathological complete response (pCR) cancer qualification when the output of the detection machine learning model comprises a pCR cancer qualification and also configured to receive a confirmed cancer quantification when the output of the detection machine learning model comprises a confirmed cancer quantification;

receiving the pCR cancer qualification when the output of the detection machine learning model comprises the pCR qualification and receiving the confirmed cancer qualification comprising one of a number of cancer cells or a density of cancer cells when the output of the detection machine learning model comprises the confirmed cancer qualification, and wherein receiving the confirmed cancer quantification also comprises receiving a type of cancer when the output of the detection machine learning model comprises a confirmed cancer quantification, wherein the type of cancer is determined based on the digital image and one or more of a tissue characteristics, slide type, glass type, tissue type, tissue region, chemical used, or stain amount, wherein the detection machine learning model comprises a treatment effect machine learning model, and wherein the treatment effect machine learning model is initialized with one of weights and/or layers from a trained version of the detection machine learning model and the treatment effect machine learning model is trained based on tagged treatment effects in the plurality of training images; and outputting the pCR cancer qualification or the confirmed cancer quantification based on the treatment effects machine learning model.

14. The non-transitory computer-readable medium of claim 13, wherein receiving the confirmed cancer quantification comprises receiving a minimal residual disease (MRD) cancer quantification.

15. The non-transitory computer-readable medium of claim 13, wherein the detection machine learning model comprises a treatment effect machine learning model.

* * * * *